(12) United States Patent
Yoshida et al.

(10) Patent No.: US 11,179,303 B2
(45) Date of Patent: Nov. 23, 2021

(54) GRANULAR COMPOSITE CONTAINING KERATIN AND HEXAGONAL PLATE-LIKE ZINC OXIDE

(71) Applicant: SAKAI CHEMICAL INDUSTRY CO., LTD., Osaka (JP)

(72) Inventors: Ryohei Yoshida, Fukushima (JP); Mitsuo Hashimoto, Fukushima (JP); Ikuhisa Nakanishi, Osaka (JP); Takahiro Domoto, Osaka (JP)

(73) Assignee: SAKAI CHEMICAL INDUSTRY CO., LTD., Osaka (JP)

( * ) Notice: Subject to any disclaimer, the term of this patent is extended or adjusted under 35 U.S.C. 154(b) by 0 days.

(21) Appl. No.: 16/766,585

(22) PCT Filed: Nov. 26, 2018

(86) PCT No.: PCT/JP2018/043349
§ 371 (c)(1),
(2) Date: May 22, 2020

(87) PCT Pub. No.: WO2019/107304
PCT Pub. Date: Jun. 6, 2019

(65) Prior Publication Data
US 2020/0368124 A1 Nov. 26, 2020

(30) Foreign Application Priority Data

Nov. 30, 2017 (JP) .............................. JP2017-230999
Nov. 30, 2017 (JP) .............................. JP2017-231000

(51) Int. Cl.
| | | |
|---|---|---|
| *A61K 8/27* | (2006.01) | |
| *A61K 8/65* | (2006.01) | |
| *A61K 8/89* | (2006.01) | |
| *A61K 47/02* | (2006.01) | |
| *A61K 47/42* | (2017.01) | |
| *A61Q 17/04* | (2006.01) | |

(52) U.S. Cl.
CPC .................. *A61K 8/27* (2013.01); *A61K 8/65* (2013.01); *A61K 8/89* (2013.01); *A61K 47/02* (2013.01); *A61K 47/42* (2013.01); *A61Q 17/04* (2013.01); *A61K 2800/412* (2013.01); *A61K 2800/61* (2013.01)

(58) Field of Classification Search
CPC ... A61K 8/27; A61K 8/65; A61K 8/89; A61K 47/02; A61K 47/42; A61K 2800/412; A61K 2800/61; A61Q 17/04
See application file for complete search history.

(56) References Cited

U.S. PATENT DOCUMENTS

| | | | |
|---|---|---|---|
| 6,296,860 B1 | 10/2001 | Hasegawa et al. | |
| 2010/0260693 A1* | 10/2010 | Kawano | A61Q 1/02 424/59 |
| 2012/0164195 A1* | 6/2012 | Zheng | A61Q 19/00 424/401 |
| 2014/0050925 A1 | 2/2014 | Sueda et al. | |
| 2016/0347624 A1 | 12/2016 | Yoshida et al. | |

FOREIGN PATENT DOCUMENTS

| | | |
|---|---|---|
| JP | H07-311189 A | 11/1995 |
| JP | H08-092035 A | 4/1996 |
| JP | 2000-212041 A | 8/2000 |
| JP | 2002-068929 A | 3/2002 |
| JP | 2003-175335 A | 6/2003 |
| WO | WO 2012/147886 A1 | 11/2012 |
| WO | WO 2015/118777 A1 | 8/2015 |

OTHER PUBLICATIONS

Garcia et al., "Controlling the Morphology of Zinc Oxide Nanorods Crystallized from Aqueous Solutions: The Effect of Crystal Growth Modifiers on Aspect Ratio," Chem. Mater. 2007, 19(16):4016-4022. (Year: 2007).*

* cited by examiner

*Primary Examiner* — Robert A Wax
*Assistant Examiner* — Olga V. Tcherkasskaya
(74) *Attorney, Agent, or Firm* — Paratus Law Group, PLLC

(57) ABSTRACT

This invention provides a material that is capable of preparing an external composition that achieves high smoothness and low roughness and that reflects near-infrared rays. Specifically, a granular composite comprising keratin and hexagonal plate-shaped zinc oxide particles is provided.

18 Claims, 10 Drawing Sheets

FIG. 6

| | Comp. Ex. 1 | Example 1 | Example 2 | Example 3 | Example 4 |
|---|---|---|---|---|---|
| Keratin structure (Number average molecular weight) | | Cationized hydrolyzed keratin (800) | Silylated hydrolyzed keratin (1200) | Hydrolyzed keratin (750) | Natural keratin (40000) |
| Amount of keratin added for the production (internal addition) | | 5 mass% | | | |
| SEM ×20000 | | | | | |
| SEM ×10000 | | | | | |
| SEM ×5000 | | | | | |
| Keratin content (mass%) | — | 1.24 | 0.88 | 0.54 | 0.61 |
| Average primary particle diameter (µm) | 0.66 | 0.67 | 0.64 | 0.63 | 0.66 |
| MB | 1.13 | 1.02 | 0.88 | 0.93 | 0.80 |
| MMD | 0.052 | 0.025 | 0.044 | 0.048 | 0.032 |

FIG. 7

| Experimental No. | Comp. Ex. 1 | Example 1 | Example 5 | Example 6 | Example 7 |
|---|---|---|---|---|---|
| Keratin structure (Number average molecular weight) | | Cationized hydrolyzed keratin (800) | | | |
| Amount of keratin added for the production | | 5 mass% | 1 mass% | 10 mass% | 20 mass% |
| SEM ×20000 | | | | | |
| SEM ×10000 | | | | | |
| SEM ×5000 | | | | | |
| Keratin content (mass%) | — | 1.24 | 0.45 | 1.41 | 1.98 |
| Average primary particle diameter (μm) | 0.66 | 0.67 | 0.70 | 0.66 | 0.70 |
| MJ | 1.13 | 1.02 | 1.12 | 1.22 | 1.17 |
| MMD | 0.0515 | 0.0252 | 0.0358 | 0.0292 | 0.0254 |

FIG. 8

| Experimental No. | Example 8 | Comp. Ex. 2 | Comp. Ex. 3 |
|---|---|---|---|
| Keratin structure (Number average molecular weight) | Hydrolyzed keratin (750) | | |
| Amount of keratin added for the production (internal addition) | 5% | | |
| SEM | ×10000 (×20000 for only Comp. Ex. 3) | | |
| | ×5000 (×10000 for only Comp. Ex. 3) | | |
| Keratin content (mass%) | 0.21% | | 0.48 |
| Average primary particle diameter (μm) | 2.15 | 2.08 | 1.04 |
| MU | 0.841 | 0.886 | |
| MVD | 0.011 | 0.0135 | 0.044 |

FIG. 9

| | XZ-1000F | Example 1a | Example 2a | Example 3a | Example 4a |
|---|---|---|---|---|---|
| Keratin structure (Number average molecular weight) | | Cationized hydrolyzed keratin (800) | Silylated hydrolyzed keratin (1200) | Hydrolyzed keratin (750) | Cationized hydrolyzed keratin (1200) |
| Amount of keratin added for the production (internal addition) | | 5 mass% | | | |
| SEM ×20000 | 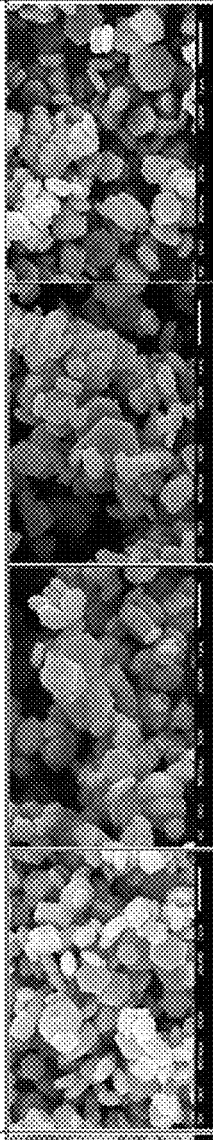 |  |  | 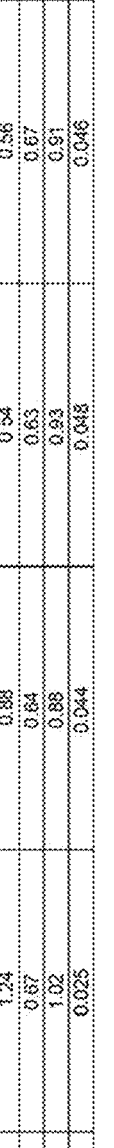 |  |
| SEM ×10000 | 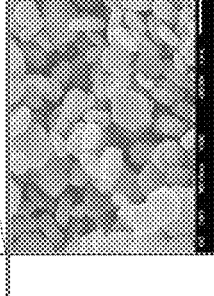 | 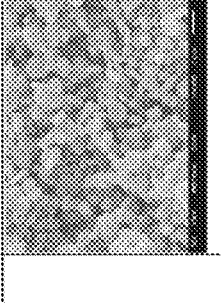 | 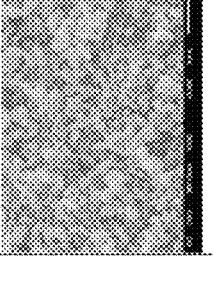 | 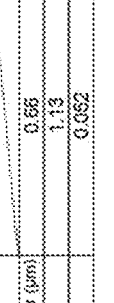 |  |
| SEM ×5000 | 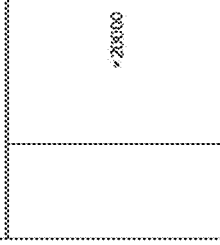 | 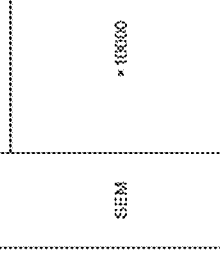 | 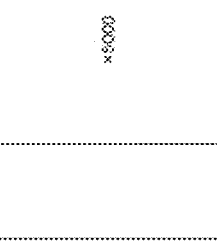 | 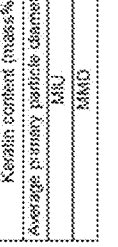 |  |
| Keratin content (mass%) | | 1.24 | 0.88 | 0.54 | 0.56 |
| Average primary particle diameter (μm) | 0.66 | 0.67 | 0.84 | 0.63 | 0.67 |
| MU | 1.13 | 1.02 | 0.88 | 0.93 | 0.91 |
| MMD | 0.052 | 0.025 | 0.044 | 0.048 | 0.046 |

FIG. 10

| | | XZ-2000F | Example A |
|---|---|---|---|
| Keratin structure (Number average molecular weight) | | | Silylated hydrolyzed keratin (1200) |
| Amount of keratin added for the production (internal addition) | | | 5 mass% |
| SEM | ×20000 | | |
| | ×10000 | | |
| | ×5000 | | |
| Average primary particle diameter (μm) | | 1.52 | 0.64 |
| MU | | 0.96 | 0.78 |
| MMD | | 0.034 | 0.020 |

GRANULAR COMPOSITE CONTAINING KERATIN AND HEXAGONAL PLATE-LIKE ZINC OXIDE

CROSS REFERENCE TO PRIOR APPLICATION

This application is a National Stage Patent Application of PCT International Patent Application No. PCT/JP2018/043349 (filed on Nov. 26, 2018) under 35 U.S.C. § 371, which claims priority to Japanese Patent Application Nos. 2017-230999 (filed on Nov. 30, 2017) and 2017-231000 (filed on Nov. 30, 2017), which are all hereby incorporated by reference in their entirety.

TECHNICAL FIELD

The present invention relates to a granular composite comprising keratin and hexagonal plate-shaped zinc oxide, and to a composition comprising the granular composite.

BACKGROUND ART

Sunlight is one of the causes of skin aging. Sunlight is composed of light of various wavelengths, including, for example, ultraviolet and near-infrared light, in addition to visible light. Since ultraviolet light has a relatively large energy, methods for reducing ultraviolet damage to skin have been developed. On the other hand, research on damage to skin caused by near-infrared light, which has a relatively small energy, has not yet particularly advanced. However, it has recently become clear that ultraviolet light is mostly absorbed at the surface layer of the skin, not reaching deep inside; while near-infrared light exerts an effect deep inside the skin, reaching the dermis and even the muscular layer. Therefore, reflecting near-infrared light to reduce sunlight damage to the skin is required.

For this purpose, incorporating into external composition a substance that has an ability to reflect near-infrared light has been studied. It is important for external compositions, which are used by applying them to the skin, to also exhibit a smooth texture (high smoothness) and roughness-free texture (low roughness) when applied. Therefore, an external composition that exhibits high smoothness and low roughness, and that reflects near-infrared light, has been required.

Additionally, industrially, a material having a high light-shielding ability is desired in various fields. If a material capable of efficiently shielding near-infrared light can be developed, this material should be applicable to various fields, in addition to the above-described external compositions, and is useful.

CITATION LIST

Patent Literature

PTL 1: WO 2012/147886
PTL 2: WO 2015/118777

SUMMARY OF INVENTION

Technical Problem

An object of the present invention is to develop a material that is capable of providing an external composition that achieves high smoothness and low roughness and that reflects near-infrared rays.

Solution to Problem

Patent Literature (PTL) 1 discloses specific hexagonal plate-shaped zinc oxide, and also discloses that the hexagonal plate-shaped zinc oxide can reflect infrared rays (including a near-infrared ray wavelength region) to some extent. The present inventors found that a granular composite obtained by subjecting hexagonal plate-shaped zinc oxide to keratin treatment has an ability to reflect near-infrared rays almost equal to or even higher than that of hexagonal plate-shaped zinc oxide itself; that the granular composite shows a relatively low MIU (mean frictional coefficient) value and a relatively low MMD (mean deviation of frictional coefficient) value; and that an external composition comprising the granular composite can thus exhibit excellent smoothness and low roughness.

The granular composite obtained by subjecting hexagonal plate-shaped zinc oxide to keratin treatment was further analyzed for whether it could be used for purposes other than external compositions. The results confirmed that granular composites obtained by subjecting hexagonal plate-shaped zinc oxide to specific keratin treatment can exhibit a particularly excellent near-infrared shielding effect when mixed with silicone to obtain a mixed composition.

For example, the present invention encompasses the subject matter stated in the following items.

Item 1. A granular composite comprising keratin and hexagonal plate-shaped zinc oxide particles.

Item 2. The granular composite according to Item 1, wherein keratin is present on the surface of the hexagonal plate-shaped zinc oxide particles.

Item 3. The granular composite according to Item 1 or 2, wherein keratin is at least one member selected from the group consisting of natural keratin, hydrolyzed keratin, cationized hydrolyzed keratin, and silylated hydrolyzed keratin.

Item 4. The granular composite according to any one of Items 1 to 3, wherein the keratin content is 0.05 to 5 mass %.

Item 5. The granular composite according to any one of Items 1 to 4, having a primary particle diameter of 0.1 to 5 µm.

Item 6. The granular composite according to any one of Items 1 to 5, wherein keratin is at least one member selected from the group consisting of cationized hydrolyzed keratin from wool, silylated hydrolyzed keratin from wool, and hydrolyzed keratin from feather; and has a number average molecular weight of 500 to 2000 g/mol.

Item 7. An external composition comprising the granular composite of any one of Items 1 to 6.

Item 8. The external composition according to Item 7, which is a cosmetic composition, a quasi-drug composition, or a pharmaceutical composition.

Item 9. A composition comprising the granular composite of Item 6 and silicone.

Item 10. The composition according to Item 9, which is a silicone film.

Advantageous Effects of Invention

The granular composite comprising keratin and hexagonal plate-shaped zinc oxide particles according to the present invention exhibits even better smoothness and lower roughness than hexagonal plate shaped zinc oxide particles themselves. Furthermore, the granular composite according to the present invention can also exhibit a near-infrared reflection effect that is almost equal to or even higher than that of hexagonal plate-shaped zinc oxide itself. For this reason, the granular composite according to the present invention can be preferably used, in particular, for example, for incorporating into an external composition.

Additionally, a specific granular composite comprising keratin and hexagonal plate-shaped zinc oxide particles can exhibit a particularly excellent near-infrared shielding effect when mixed with silicone to obtain a mixed composition.

BRIEF DESCRIPTION OF DRAWINGS

FIG. 6 shows SEM photographs and experimental analytical results.

FIG. 7 shows SEM photographs and experimental analytical results.

FIG. 8 shows SEM photographs and experimental analytical results.

FIG. 9 shows SEM photographs and experimental measurement results.

FIG. 10 shows SEM photographs and experimental measurement results.

DESCRIPTION OF EMBODIMENTS

Figure 1:
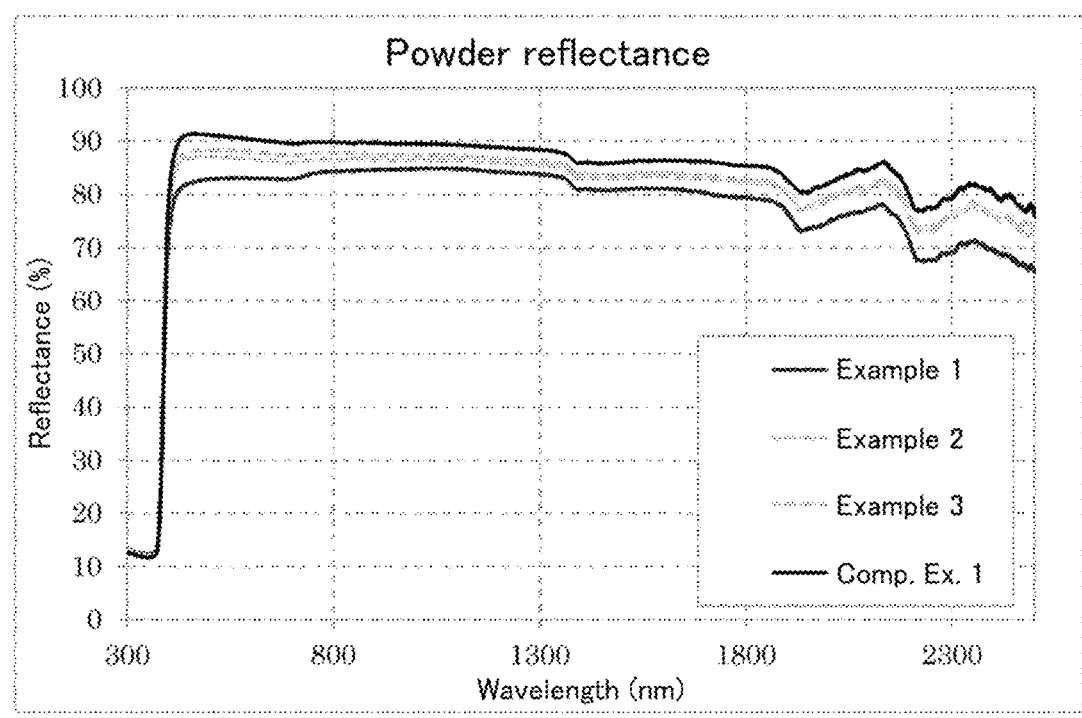
FIG. 1 is a graph showing the measurement results of spectral reflectance of granular composites comprising keratin and hexagonal plate-shaped zinc oxide particles, and hexagonal plate-shaped zinc oxide particles themselves.

Below, each embodiment of the present invention is described in further detail.

The granular composite encompassed by the present invention comprises keratin and hexagonal plate-shaped zinc oxide particles.

Keratin is not particularly limited, and may be any of various known keratins particularly for use as cosmetic materials (e.g., skin conditioning agents and hair conditioning agents). Examples of such keratins include natural keratin, hydrolyzed keratin, cationized hydrolyzed keratin, silylated hydrolyzed keratin, and the like. Examples of hydrolyzed keratin include those obtained by subjecting a keratin protein to hydrolysis with an acid, an alkali, an enzyme, or the like. Cationized hydrolyzed keratin or silylated hydrolyzed keratin can be prepared by cationizing or silylating hydrolyzed keratin with a denaturing agent etc., or by hydrolyzing a cationized keratin protein or silylated keratin protein that has been denatured beforehand. Examples of the cationized hydrolyzed keratin include hydroxypropyltrimonium hydrolyzed keratin, steardimonium hydroxypropyl hydrolyzed keratin, lauryldimonium hydroxypropyl hydrolyzed keratin, and the like. Examples of the silylated hydrolyzed keratin include (dihydroxymethylsilylpropoxy)hydroxypropyl hydrolyzed keratin, and the like.

The average molecular weight (molecular weight herein is reported in the units of g/mol) of keratin is not particularly limited, and is preferably, for example, about 100 to 50000, and more preferably about 200 to 40000. Keratin is preferably hydrolyzed to have a reduced average molecular weight; for example, the average molecular weight is preferably about 300 to 5000, more preferably about 400 to 3000, and still more preferably about 500 to 2000. The average molecular weight represents a number average molecular weight. Cosmetic material manufacturers provide number average molecular weight values for commercial products. These number average molecular weight values provided by the manufacturers can be preferably used as the average molecular weight of keratin in the present invention.

The raw material of keratin is also not particularly limited. Various keratins known for use as a cosmetic material are prepared, for example, from wool or feather; thus, in the present invention as well, keratin prepared from wool or feather can be preferably used.

When the granular composite is used by mixing with silicone rubber, the keratin contained in the granular composite is preferably cationized hydrolyzed keratin from wool, silylated hydrolyzed keratin from wool, or hydrolyzed keratin from feather. In this case, keratin preferably has an average molecular weight of 500 to 2000, more preferably 600 to 1800, and still more preferably 700 to 1500. The average molecular weight represents a number average molecular weight as described above.

The keratins may be used alone, or in a combination of two or more.

The hexagonal plate-shaped zinc oxide particles preferably has a primary particle diameter of 0.1 to 10 μm, more preferably 0.1 to 5 μm still more preferably 0.2 to 4 μm and even more preferably 0.5 to 3 μm. With the primary particle diameter within this range, high smoothness and low roughness, as well as a further excellent near-infrared reflection effect, can be obtained.

The primary particle diameter of hexagonal plate-shaped zinc oxide particles is a value calculated from 50% in the cumulative distribution obtained by measuring the diagonal diameter (μm) of 100 particles in the visual field of a photograph taken at 2000 to 50000-fold magnification with a scanning electron microscope (SEM) (e.g., JSM-6510A; produced by JEOL Ltd.) (a length of a single diagonal line arbitrarily selected from three diagonal lines of the hexagonal plate-shaped surface).

The hexagonal plate-shaped zinc oxide particles preferably have an aspect ratio of 2.5 or more. The aspect ratio 2.5 is more preferably 2.7 or more, and still more preferably 3.0 or more. With the plate shape having an aspect ratio of 2.5 or more, higher smoothness, lower roughness, as well as a higher near-infrared reflection effect, can be obtained.

The aspect ratio is a value determined as a ratio of L/T, wherein L represents an average value of the diagonal diameters (μm) of 100 hexagonal plate-shaped zinc oxide particles whose hexagonal plate-shape surface is facing frontward in the visual field of a photograph taken at 2000 to 50000-fold magnification with a scanning electron microscope (SEM) (e.g., JSM-6510A; produced by JEOL Ltd.) (for hexagonal plate-shaped zinc oxide particles, a length of a single diagonal line arbitrarily selected from three diagonal lines of the hexagonal plate-shaped surface); and T represents an average value of the thicknesses (μm) of 100 hexagonal plate-shaped zinc oxide particles whose side surface is facing frontward (particles apparently having a rectangular shape) (a length of the shorter side of the rectangle).

The hexagonal plate-shaped zinc oxide particles are disclosed, for example, in WO2012/147886 and WO2015/118777; and can be produced, for example, by the methods disclosed in these documents. More specifically, for example, the hexagonal plate-shaped zinc oxide particles can be obtained by a production method comprising a step of aging zinc oxide fine particles in a zinc salt aqueous solution. This production method is described in detail below.

The zinc oxide fine particles are not particularly limited, and it is preferable to use raw zinc oxide having a particle diameter of 0.005 μm or more and 0.2 μm or less. The particle diameter of the raw zinc oxide corresponds to the diameter of a sphere having a surface area equal to the specific surface area determined by a Brunauer-Emmett-Teller (BET) method. That is, the particle diameter is a value calculated by the following formula, wherein Sg represents a specific surface area determined by a BET method, and ρ represents the true specific gravity of zinc oxide. The measurement with a BET method may be performed by using a full automatic BET specific surface area analyzer (e.g., MACSORB, Model HM-1200, produced by Mountech Co., Ltd.).

$$\text{Particle diameter (μm)} = [6/(Sg \times \rho)]$$

(Sg (m$^2$/g): specific surface area, ρ (g/cm$^3$): true specific gravity of particles)

In this calculation, ρ (true specific gravity of particles) is 5.6, which is the true specific gravity value of zinc oxide.

The raw zinc oxide is not particularly limited, and zinc oxide produced by a known method can be used. Examples of commercially available products include FINEX-75, FINEX-50, FINEX-30, SF-15, and fine zinc oxide, all of which are produced by Sakai Chemical Industry Co., Ltd.

The hexagonal plate-shaped zinc oxide particles can be obtained by aging the zinc oxide fine particles in a zinc salt aqueous solution. Specifically, the hexagonal plate-shaped zinc oxide particles can be obtained by dispersing the zinc oxide fine particles in a zinc salt aqueous solution, performing heating in that state, and allowing the crystals to grow.

The zinc salt in the zinc salt aqueous solution is not particularly limited. Examples include zinc salt compounds, such as zinc acetate, zinc nitrate, zinc sulfate, zinc chloride, and zinc formate. From the selections of zinc salt aqueous solutions, in particular, when a zinc acetate aqueous solution is used, the specific hexagonal plate-shaped zinc oxide particles of the present invention are suitably obtained.

These zinc salt aqueous solutions may also be prepared by mixing zinc oxide, an acid, and water; and subjecting the zinc oxide to acid hydrolysis. The particle shape and particle diameter of the zinc oxide used in the preparation of the zinc salt aqueous solution by using zinc oxide, an acid, and water are not particularly limited. To minimize the formation of impurities, the Zn purity of the zinc oxide is preferably 95% or more. Examples of the acid include acetic acid, nitric acid, sulfuric acid, hydrochloric acid, formic acid, citric acid, oxalic acid, propionic acid, malonic acid, lactic acid, tartaric acid, gluconic acid, succinic acid, and the like. In particular, when acetic acid is used, the specific hexagonal plate-shaped zinc oxide particles of the present invention are suitably obtained. These zinc salt aqueous solutions may be used in a combination of two or more.

The zinc salt concentration in the zinc salt aqueous solution is preferably more than 0.1 mol/l and 4.0 mol/l or less. In particular, when an aqueous zinc acetate solution is used, the zinc acetate concentration in the aqueous solution is preferably more than 0.2 mol/l and 2.0 mol/l or less.

The zinc salt aqueous solution may contain a small amount of components other than the zinc salt and water, as long as the effects of the present invention are not impaired. For example, the zinc salt aqueous solution may further contain a dispersant etc.

When zinc oxide fine particles are added to the zinc salt aqueous solution to obtain a slurry, the concentration of zinc oxide fine particles based on the total amount of the slurry is preferably 10 to 500 g/l.

For the acing above, a small amount of components other than the zinc oxide fine particles, zinc salt, and water may be added, as long as the effects of the present invention are not impaired. For example, a dispersant etc. may be added.

Aging is preferably performed at 45 to 110° C. The aging time can be 0.5 to 24 hours. The particle diameter can be adjusted according to the conditions, such as the aging temperature, aging time, concentration of the raw zinc oxide, and concentration of the zinc salt. Therefore, these conditions are preferably set appropriately according to the target hexagonal plate-shaped zinc oxide particles.

The thus-obtained hexagonal plate-shaped zinc oxide particles may be optionally subjected to post-treatment, such as filtration, washing with water, and drying.

The hexagonal plate-shaped zinc oxide particles produced by the above method may be optionally classified. Examples of the classification include classification using a sieve. Examples of the classification using a sieve include wet classification and dry classification. Additionally, wet pulverization, dry pulverization, or other treatment may also be performed.

Although the production method described above is capable of producing hexagonal plate-shaped zinc oxide particles without firing treatment, the hexagonal plate-shaped zinc oxide particles obtained by the above method may be subjected to firing treatment. Firing may be performed by a method using any known apparatus, and the treatment conditions and the like are also not particularly limited.

The hexagonal plate-shaped zinc oxide particles may also be a commercially available product. For example, hexagonal plate-shaped zinc oxide XZ series, produced by Sakai Chemical Industry Co., Ltd., can be preferably used. Of these, XZ-1000F, XZ-2000F, XZ-3000F, etc., are more preferably used. The average particle diameters shown in the catalogs of these commercially available products are values measured by a laser-diffraction particle diameter distribution measuring apparatus, and are different from the values of the average particle diameter used in the present invention.

The hexagonal plate-shaped zinc oxide particles can be used alone, or in a combination of two or more.

The granular composite according to the present invention comprises keratin and hexagonal plate-shaped zinc oxide particles. It is preferable that keratin be provided on the surface of the hexagonal plate-shaped zinc oxide particles. In particular, it is preferable that keratin be present on the plate surface of the hexagonal plate-shaped zinc oxide particles.

Examples of a method of providing keratin on the surface of the hexagonal plate-shaped zinc oxide particles (in other words, a method of treating the surface of the hexagonal plate-shaped zinc oxide particles with keratin) include a method comprising a step of drying a slurry containing hexagonal plate-shaped zinc oxide particles and keratin. More specifically, for example, a granular composite in which keratin is provided on the surface of hexagonal plate-shaped zinc oxide particles can be obtained by mixing hexagonal plate-shaped zinc oxide and water to prepare a slurry; adding a specific amount of keratin (such that, for example, the amount of keratin added is 0.5 to 10 mass % or about 1 to 8 mass %, based on the total amount of zinc oxide and keratin) while stirring the slurry; aging the resulting mixture for a specific period of time (e.g., about 30 to 120 minutes); optionally performing filtration and washing with water; and further drying the resulting product (e.g., at about 30 to 50° C. for about 12 to 24 hours).

The keratin content of the granular composite according to the present invention is preferably 0.05 to 5 mass %, more preferably 0.8 to 4 mass %, and still more preferably 0.1 to 3 mass %. The presence of keratin in the above percentage can achieve more excellent effects; i.e., more smoothness, less roughness, and better infrared reflectivity. The lower limit of the keratin content may be 0.2, 0.3, 0.4, or 0.5 mass %. The upper limit of the keratin content may be 2.5, 2, or 1.5 mass %. The keratin content of the granular composite is a value obtained as follows. Specifically, 2 g each of the granular composite and hexagonal plate-shaped zinc oxide particles (a raw material of the granular composite) are separately placed into a crucible, and heated at 500° C. for 1 hour in an electric furnace, followed by measuring the weights after heating. Then, the keratin content (mass %) of the granular composite is calculated, assuming that the keratin contained in the granular composite completely disappeared, and that the reduction rate of the hexagonal zinc oxide particles (raw material) is the same in both of these cases.

In the granular composite according to the present invention, keratin is preferably provided on the surface. The granular composite may consist of hexagonal plate-shaped zinc oxide particles and keratin; or may comprise hexagonal plate-shaped zinc oxide particles, keratin, and a component other than these, as long as the effects of the present invention are not impaired. However, it is preferable that keratin is present on part or the entire surface of the composite. Further, the granular composite itself preferably has a hexagonal plate shape. Additionally, for example, it is preferable that the hexagonal plate-shaped zinc oxide particles and keratin form a laminate. Further, it is preferable that the surface of the hexagonal plate-shaped zinc oxide particles be treated with keratin, and that keratin be immobilized on the surface. Although a restrictive interpretation is not desired, when the composite itself has a hexagonal plate shape, it is assumed that the composite can be spread in a plane while forming no large gap. Further, when the composite is spread such that the keratin-treated surface is on the front surface, it is assumed that the keratin-treated surface is formed on the front of the plane in which the composite is spread.

When a component other than the hexagonal plate-shaped zinc oxide particles and keratin is contained in the granular composite, it is preferable that the component be present between the hexagonal plate-shaped zinc oxide particles and keratin. For example, when hexagonal plate-shaped zinc oxide particles that have been surface-treated with other components are subjected to keratin treatment to prepare the granular composite, the other components (components used for the surface treatment performed beforehand on the surface of the hexagonal plate-shaped zinc oxide particles) will be present between the hexagonal plate-shaped zinc oxide particles and keratin.

In this specification, the concept of the granular composite comprising keratin on the surface of hexagonal plate-shaped zinc oxide particles also encompasses granular composites comprising other components between the hexagonal plate-shaped zinc oxide particles and keratin. In other words, as long as keratin is provided on the surface of the granular composite, the granular composite comprising keratin on the surface of hexagonal plate-shaped zinc oxide particles may be those in which keratin is present in contact with the surface of the hexagonal plate-shaped zinc oxide particles, or those in which other components are present between keratin and the surface of the hexagonal plate-shaped zinc oxide particles.

The surface treatment that may be applied to the surface of the hexagonal plate-shaped zinc oxide particles beforehand is not particularly limited. Examples include surface treatment to form a layer of at least one compound selected from the group consisting of silicon oxides, silicon oxide hydrates, aluminum oxides, and aluminum hydroxides; surface treatment with water-repellent organic compounds; and surface treatment with a coupling agent, such as a silane coupling agent or a titanium coupling agent. These surface treatments may be performed in combination of two or more.

The formation of a layer of at least one compound selected from the group consisting of silicon oxides, silicon oxide hydrates, aluminum oxides, and aluminum hydroxides can be per by a method of, for example, depositing an Si source compound and/or an Al source compound on the powder surface thorough hydrolysis, thermolysis, or the like. The Si source compound and/or Al source compound include compounds that are easily converted into $SiO_2$, $Al(OH)_3$, or $Al_2O_3$, such as tetraalkoxysilane or a hydrolysis condensate thereof, sodium silicate, potassium silicate, aluminum alkoxide or a hydrolysis condensate thereof, and sodium aluminate.

The hydrolysis is not particularly limited. Examples of the method include a method that uses an acid, such as sulfuric acid, hydrochloric acid, acetic acid, and nitric acid. The neutralization method in the silica treatment method using aqueous dispersion may be any of the following: a method of adding an acid to the dispersion containing hexagonal plate-shaped zinc oxide particles, and then adding the Si source compound and/or Al source compound; a method of adding an acid after adding the Si source compound and/or Al source compound to the dispersion; and a method of simultaneously adding the Si source compound and/or Al source compound, and an acid, to the dispersion.

The treatment with a water-repellent organic compound is not particularly limited. Examples include a treatment using silicone oils, alkyl silanes, alkyl titanates, alkyl aluminates, polyolefins, polyesters, metal soaps, amino acids, amino acid salts, and the like. Among these, silicone oils are preferable in terms of chemical stability. Specific examples of the silicone oils include dimethyl polysiloxane (e.g., KF-96A-100cs, produced by Shin-Etsu Chemical Co., Ltd. and DM10, produced by Wacker Asahikasei Silicone Co., Ltd.), methyl hydrogen polysiloxane (e.g., KF-99P, produced by Shin-Etsu Chemical Co., Ltd. and SH1107C, produced by Toray Dow Corning Silicone Co., Ltd.), (dimethicone/methicone) copolymers (e.g., KF-9901, produced by Shin-Etsu Chemical Co., Ltd.), methylphenyl silicone (e.g., KF-50-100cs, produced by Shin-Etsu Chemical Co., Ltd.), amino-modified silicone (e.g., KF-8015, produced by Shin-Etsu Chemical Co., Ltd., JP-8500 Conditioning Agent, produced by Toray Dow Corning Silicon Co., Ltd., and ADM6060, produced by Wacker Asahikasei Silicone Co., Ltd.), triethoxysilylethyl polydimethylsiloxyethyl dimethicone (e.g., KF-9908, produced by Shin-Etsu Chemical Co., Ltd.), triethoxysilylethyl polydimethylsiloxyethyl hexyl dimethicone (e.g., KF-9909, produced by Shin-Etsu Chemical Co., Ltd.), and the like.

The treatment, with a silane coupling agent may be performed using vinyl tris(2-methoxyethoxy)silane, vinyltrichlorosilane, vinyltrimethoxysilane, vinyltriethoxysilane, 2-(3,4 epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, N-2(aminoethyl)3-aminopropylmethyldimethoxysilane, N-2(aminoethyl)3-aminopropyltriethoxysilane, N-2(aminoethyl)3-aminopropyltriethoxysilane, 3-aminotriethoxysilane, 3-triethoxysilyl-N-(1, 3-dimethyl-butylidene)propylamine, N-phenyl-3-aminopropyltrimethoxysilane, N-(vinylbenzyl)-2-aminoethyl-3-aminopropyltrimethoxysilane hydrochloride, 3-ureidopropyltriethoxysilane, 3-chloropropyltrimethoxysilane, 3-mercaptopropylmethyldimethoxysilane, 3-mercaptopropyltrimethoxysilane, bis(triethoxysilylpropyl)tetrasulfide, 3-isocyanatepropyltriethoxysilane, tetramethoxysilane, tetraethoxysilane, methyltrimethoxysilane, methyltriethoxysilane, phenyltriethoxysilane, hexamethyldisilazane, hexyltrimethoxysilane, and decyltrimethoxysilane.

The treatment with a titanium coupling agent may be performed using tetraisopropyl titanate, tetra-n-butyl titanate, butyltitanate dimer, tetra(2-ethylhexyl)titanate, tetramethyl titanate, titanium acetylacetonate, titanium tetraacetylacetonate, titanium ethylacetoacetate, titanium octanediolate, titanium lactate, titanium triethanolaminato, and polyhydroxy titanium stearate.

When the above surface treatment (surface treatment performed beforehand on the surface of hexagonal plate-shaped zinc oxide particles, prior to keratin treatment) is performed, 0.1 to 30 wt % of the powder is preferably surface-treated, based on the total amount of the powder after treatment. It is preferable to adjust the amount within this range to improve smoothness, the humidity resistance, and the dispersibility in resin.

The primary particle diameter of the granular composite according to the present invention is preferably equivalent to the primary particle diameter of the hexagonal plate-shaped zinc oxide particles described above. In particular, the primary particle diameter is preferably 0.1 to 5 μm, more preferably 0.2 to 4 μm, and still more preferably 0.5 to 3 μm. When the primary particle diameter is within this range, higher smoothness, lower roughness, and a more excellent near-infrared reflection effect are obtained. The upper limit may also be 2.5 μm, 2 μm, 1.5 μm, or 1 μm.

The primary particle diameter of a granular composite is a value calculated from 50% in the cumulative distribution obtained by measuring the diagonal diameter (μm) of 100 particles in the visual field of a photograph taken at 2000 to 50000-fold magnification with a scanning electron microscope (SEM) (e.g., JSM-6510A; produced by JEOL Ltd.) (in particular, if the granular composite has a hexagonal plate shape, then a length of a single diagonal line arbitrarily selected from three diagonal lines of the hexagonal plate-shaped surface).

The granular composite according to the present invention preferably has an aspect ratio of 2.5 or more. The aspect ratio is more preferably 2.7 or more, and still more preferably 3.0 or more. With the plate shape having an aspect ratio of 2.5 or more, the granular composite exhibits higher smoothness, lower roughness, as well as a higher-near infrared reflection effect.

When the granular composite has a hexagonal plate shape, the aspect ratio is a value determined as a ratio of L/T, wherein L represents an average value of the diagonal diameters (μm) of 100 particles whose hexagonal plate-shaped granular composite surface is facing frontward in the visual field of a photograph of the hexagonal plate-shaped granular composite taken at 2000 to 50000-fold magnification with a scanning electron microscope (SEM) (a length of a single diagonal line arbitrarily selected from three diagonal lines of the hexagonal plate-shaped surface); and T represents an average value of the thicknesses (μm) of 100 hexagonal plate-shaped granular composite particles whose side surface is facing frontward (particles apparently having a rectangular shape) (a length of the shorter side of the rectangle).

The granular composite according to the present invention can achieve excellent smoothness and low roughness, for example, when incorporated in an external composition. Specifically, the granular composite (powder) according to the present invention shows a small MIU (mean frictional coefficient) value and a small MMD (mean deviation of frictional coefficient) value. A smaller MIU (mean frictional coefficient) value represents smoother texture with better smoothness. A smaller MMD (mean deviation of frictional coefficient) value represents less roughness. The comparison target here is hexagonal plate-shaped zinc oxide particles themselves used as a raw material of the granular composite. More specifically, the granular composite (powder) according to the present invention has a smaller MIU (mean frictional coefficient) value and a smaller MMD (mean deviation of frictional coefficient) value, compared to the hexagonal plate-shaped zinc oxide particles (powder) used as a raw material of the granular composite.

For example, although not particularly limited, the granular composite (powder) according to the present invention has an MIU value of preferably 1.15 or less, more preferably 1.1 or less, and still more preferably 1.05 or less. Further, the MMD value is preferably 0.05 or less. The MMD value is more preferably 0.04 or less, or 0.03 or less. It is particularly preferable to satisfy both of these MIU and MMD values.

The MIU value and the MMD value are measured as follows. More specifically, the MIU and MMD values are obtained by measurement using a friction tester (e.g., KES-SE friction tester, produced by Kato Tech Co., Ltd.), with respect to a granular composite (powder) spread on a double-sided tape under the conditions of a friction measurement load of 25 gf, a surface measurement sample moving speed of 1 mm/sec, and a measurement distance range of 20 mm.

The granular composite according to the present invention may be mixed with other components and incorporated into, for example, an external composition (e.g., a drug, a quasi-drug, and a cosmetic), an ink, a paint, a plastic, and the like. In particular, considering the above-described properties, the granular composite is preferably incorporated into an external compositor to achieve excellent powder texture, i.e., excellent smoothness and low roughness. Of the above, the granular composite is suitably used by incorporating in cosmetics.

The cosmetics are not particularly limited. By mixing the above powder with cosmetic raw materials as necessary, it is possible to obtain UV-protective cosmetics, such as sunscreen agents; base makeup cosmetics, such as foundations; point makeup cosmetics, such as lipsticks; skin care cosmetics, such as lotions and creams; hair care cosmetics, such as treatments and styling agents; and the like. Further, the hexagonal plate-shaped zinc oxide particles of the present invention, which exhibit not only excellent powder texture as stated above but also UV absorbing ability, show excellent performance when used in cosmetics. The cosmetics can be in any form, such as oil-based cosmetics, water-based cosmetics, O/W cosmetics, W/O cosmetics, and the like.

The cosmetics may also contain any water-based component or oil-based component that is usable in the cosmetic field. The water-based component and the oil-based component are not particularly limited; and may be, for example, those that contain components, such as oil solutions, surfactants, humectants, higher alcohols, sequestering agents, natural or synthetic polymers, water-soluble or oil-soluble polymers, ultraviolet shielding agents, various extracts, coloring agents (e.g., organic dyes), preservatives, antioxidants, pigments, thickeners, pH adjusters, perfumes, cooling agents, antiperspirants, bactericidal agents, skin activators, and various powders.

Examples of the oil solutions include, but are not particularly limited to, natural animal and vegetable oils and fats (e.g., olive oil, mink oil, castor oil, palm oil, beef tallow, evening primrose oil, coconut oil, castor oil, cacao oil, and macadamia nut oil); waxes (e.g., jojoba oil, beeswax, lanolin, carnauba wax, and candelilla wax); higher alcohols (e.g., lauryl alcohol, stearyl alcohol, cetyl alcohol, and oleyl alcohol); higher fatty acids (e.g., lauric acid, palmitic acid, stearic acid, oleic acid, behenic acid, and lanolin fatty acid); higher aliphatic hydrocarbons (e.g., liquid paraffin, solid paraffin, squalane, Vaseline, ceresin, and microcrystalline wax); synthetic ester oils (e.g., butyl stearate, hexyl laurate, diisopropyl adipate, diisopropyl sebacate, octyldodecyl myristate, isopropyl myristate, isopropyl palmitate, isopropyl myristate, cetyl isooctanoate, and neopentyl glycol dicaprate); silicone derivatives (e.g., silicone oils, such as methyl silicone and methyl phenyl silicone); and the like. Further, oil-soluble vitamins, preservatives, whitening agents, and the like may also be incorporated.

Examples of the surfactants include lipophilic nonionic surfactants, hydrophilic nonionic surfactants, and the like. Examples of the lipophilic nonionic surfactants include, but are not particularly limited to, sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerol fatty acids, such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters, such as propylene glycol monostearate; hydrogenated castor oil derivatives; glycerol alkyl ethers; and the like.

Examples of the hydrophilic nonionic surfactants include, but not particularly limited to, POE sorbitan fatty acid esters, such as POE sorbitan monooleate, POE sorbitan monostearate, and POE sorbitan tetraoleate; POE sorbit fatty acid esters, such as POE sorbit monolaurate, POE sorbit monooleate, POE sorbit pentaoleate, and POE sorbit monostearate; POE glycerol fatty acid esters, such as POE glycerol monostearate, POE glycerol monoisostearate, and POE glycerol triisostearate; POE fatty acid esters, such as POE monooleate, POE distearate, POE dioleate, and ethylene glycol distearate; POE alkyl ethers, such as POE lauryl ether, POE oleyl ether, POE stearyl ether, POE behenyl ether, POE 2-octyl dodecyl ether, and POE cholestanol ether; POE alkyl phenyl ethers, such as POE octyl phenyl ether, POE nonyl phenyl ether, and POE dinonyl phenyl ether; Pluronic-type surfactants, such as Pluronic; POE/POP alkyl ethers, such as POE/POP cetyl ether, POE/POP2-decyl tetradecyl ether, POE/POP monobutyl ether, POE/POP hydrogenated lanolin, and POE/POP glycerin ether, tetra POE/tetra POP ethylenediamine condensation products, such as Tetronic; POE castor oil hydrogenated castor oil derivatives, such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives, such as POE sorbit beeswax; alkanolamide, such as coconut oil fatty acid diethanolamide, lauric acid monoethanolamide, and fatty acid isopropanolamide; POE propylene glycol fatty acid esters; POE alkylamines; POE fatty acid amides; sucrose fatty acid esters; POE nonyl phenyl formaldehyde condensation products; alkyl ethoxydimethylamine oxides; trioleyl phosphate; and the like.

Other surfactants may also be added, as long as they do not cause problems with respect to stability and skin irritation. Examples include anionic surfactants, such as fatty acid soaps, higher alkyl sulfate ester salts, POE lauryl sulfate triethanolamine, and alkyl ether sulfate ester salts; cationic surfactants, such as alkyl trimethyl ammonium salts, alkyl pyridinium salts, alkyl quaternized ammonium salts, alkyl dimethyl benzylammonium salts, POE alkylamines, alkylamine salts, and polyamine fatty acid derivatives; amphoteric surfactants, such as imidazoline-based amphoteric surfactants and betaine-based surfactants; and the like.

Examples of the humectants include, but are not particularly limited to, xylitol, sorbitol, maltitol, chondroitin sulfate, hyaluronic acid, mucoitinsulfuric acid, caronic acid, atelocollagen, cholesteryl-12-hydroxystearate, sodium lactate, bile salt, dl-pyrrolidone carboxylate salt, short-chain soluble collagen, diglycerin (EO)PO adducts, *Rosa roxburghii* extract, yarrow extract, melilot extract, and the like.

Examples of the higher alcohols include, but are not particularly limited to, linear alcohols, such as lauryl alcohol, cetyl alcohol, stearyl alcohol, behenyl alcohol, myristyl alcohol, oleyl alcohol, and cetostearyl alcohol; and branched alcohols, such as monostearyl glycerin ether (batyl alcohol), 2 decyl tetradecinol, lanolin alcohol, cholesterol, phytosterol, hexyldodecanol, isostearyl alcohol, octyl dodecanol, and the like.

Examples of the sequestering agents include, but are not particularly limited to, 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, edetic acid, and the like.

Examples of the natural water-soluble polymers include, but are not particularly limited to, plant polymers, such as gum arabic, tragacanth gum, galactan, guar gum, carob gum, karaya gum, carrageenan, pectin, agar, quince seed (*Cydonia oblonga*), algae colloid (brown algae extract), starch (rice, corn, potato, wheat), and glycyrrhizinic acid; microbial polymers, such as xanthan gum, dextran, succinoglycan, and pullulan; and animal polymers, such as collagen, casein, albumin, and gelatin.

Examples of the semisynthetic water-soluble polymers include, but are not particularly limited to, starch polymers, such as carboxymethyl starch and methyl hydroxypropyl starch; cellulose polymers, such as methylcellulose, nitrocellulose, ethylcellulose, methyl hydroxypropyl cellulose, hydroxyethyl cellulose, cellulose sodium sulfate, hydroxypropyl cellulose, sodium carboxymethyl cellulose (CMC), crystalline cellulose, and cellulose powder; and alginate polymers, such as sodium alginate and alginic acid propylene glycol ester.

Examples of the synthetic water-soluble polymers include, but are not particularly limited to, vinyl polymers, such as polyvinyl alcohol, polyvinyl methyl ether, and polyvinylpyrrolidone; polyoxyethylene polymers, such as polyethylene glycols 20,000, 40,000, and 60,000; copolymers, such as polyoxyethylene polyoxypropylene copolymers; acrylic polymers, such as sodium polyacrylate, polyethyl acrylate, and polyacrylamide; polyglycerin, polyethylenimine, cationic polymer, carboxyvinyl polymer, alkyl-modified carboxyvinyl polymer, (hydroxyethyl acrylate/acryloyl dimethyl taurine Na)copolymer, (acrylate Na/acryloyl dimethyl taurine Na)copolymer, (acryloyl dimethyl taurine ammonium/vinylpyrrolidone)copolymer, (acryloyl dimethyl taurine ammonium methacrylate beheneth-25)crosspolymer, and the like.

Examples of the inorganic water-soluble polymers include, but are not particularly limited to, bentonite, magnesium aluminum silicate (Veegum), laponite, hectorite, and silicic anhydride.

Examples of the ultraviolet shielding agents include, but are not particularly limited to, benzoic acid-based ultraviolet shielding agents, such as p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based ultraviolet shielding agents, such as homomenthyl-N-acetyl anthranilate; salicylic acid-based ultraviolet shielding agents, such as amyl salicylate, menthyl salicylate, homomenthyl salicylate, octyl salicylate, phenyl salicylate, benzyl salicylate, and p-isopropanol phenyl salicylate; cinnamic acid-based ultraviolet shielding agents, such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-diparamethoxy cinnamate; benzophenone-based ultraviolet shielding agents, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methyl benzophenone, 2-hydroxy-4-methoxybenzophenone-5-sulfonate, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methyl benzoxazole, 2,2'-hydroxy-5-methyl phenyl benzotriazole, 2-(2'-hydroxy-5'-t-octylphenyl)benzotriazole, 2-(2'-hydroxy-5'-methylphenyl) benzotriazole, dibenzalazine, dianisoylmethane, 4-methoxy-4'-t-butyldibenzoylmethane, and 5-(3,3-dimethyl-2-norbornylidene)-3-pentan-2-one; and the like.

Examples of the other chemical components include, but are not particularly limited to, vitamins, such as vitamin A oil, retinal, retinol palmitate, inositol, pyridoxine hydrochloride, benzyl nicotinate, nicotinamide, dl-α-tocopherol nicotinate, magnesium ascorbyl phosphate, 2-O-α-D-glucopyranosyl-L-ascorbic acid, vitamin D2 (ergocalciferol), dl-α-tocopherol, di-α-tocopherol acetate, pantothenic acid, and biotin; hormones, such as estradiol and ethinyl estradiol; amino acids such as arginine, aspartic acid, cystine, cysteine, methionine, serine, leucine, and tryptophan; anti-inflammatory agents, such as allantoin and azulene; whitening agents, such as arbutin; astringents, such as tannic acid; refrigerants, such as L-menthol and camphor; sulfur, lysozyme chloride, and pyridoxine chloride; and the like.

Examples of various extracts include, but are not particularly limited to, Houttuynia cordata extract, phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, each leaf extract, mulberry extract, knapweed extract, hamamelis extract, placenta extract, thymic extract, silk extract, licorice extract, and the like.

Examples of various powders include luster color pigments, such as red iron oxide, yellow iron oxide, black iron oxide, mica titanium, iron oxide-coated mica titanium, and titanium oxide-coated glass flake; inorganic powders, such as mica, talc, kaolin, sericite, titanium dioxide, and silica; organic powders, such as polyethylene powder, nylon powder, crosslinked polystyrene, cellulose powder, and silicone powder; and the like. In order to improve sensory characteristics and makeup retainability, some or all of the powder components are preferably hydrophobized with a material such as a silicone, a fluorine compound, a metal soap, an oil solution, or an acyl glutamic acid salt, by a known method. Further, a composite powder other than the composite powders of the present invention may also be mixed and used.

When the granular composite according to the present invention is used as a component for addition to inks, the granular composite can be used in combination with colored pigments, such as titanium oxide, red iron oxide, antimony red, cadmium yellow, cobalt blue, Prussian blue, ultramarine, carbon black, and graphite; and extender pigments, such as calcium carbonate, kaolin, clay, barium sulfate, aluminum hydroxide, and talc. Further, the granular composite can also be used in combination with organic pigments including pigment components, such as soluble azo pigments, insoluble azo pigments, azo lake pigments, condensed azo pigments, copper phthalocyanine pigments, and condensed polycyclic pigments; binder resins, such as shellac resin, acrylic resin, styrene-acrylic resin, styrene-maleic acid resin, styrene-acrylic-maleic acid resin, polyurethane resin, polyester resin, and polyamide resin; water-miscible organic solvents; and the like.

When the granular composite according to the present invention is used as a component for addition to paint compositions, the granular composite can be used in combination with film-forming resins, such as acrylic resin, polyester resin, and epoxy resin; various pigments, such as color pigments, extender pigments, and luster pigments; curing catalysts, surface control agents, antifoaming agents, pigment dispersants, plasticizers, film-forming aids, ultraviolet absorption agents, and antioxidants; and the like. The resin in the paint may be curable, or may not be curable.

The present invention also encompasses a resin composition comprising the granular composite of the present invention described above. This resin composition has excellent heat dissipation properties, since the granular composite functions as a heat dissipation filler. Further, infrared (in particular, near-infrared) reflectivity is excellent; therefore, the resin composition can also be used as a resin composition having these properties.

As described above, the hexagonal plate-shaped zinc oxide particles according to the present invention has infrared (in particular, near-infrared) reflectivity, and can thus also be used as an infrared (in particular, near-infrared) shielding material in various fields.

Further, when the keratin in the granular composite comprising keratin and the hexagonal plate-shaped zinc oxide particles according to the present invention is a specific keratin, a particularly excellent near-infrared shielding effect can be exhibited when mixed with silicone (in particular, silicone rubber) to be used as a silicone composition. The specific keratin may be, for example, cationized hydrolyzed keratin from wool, silylated hydrolyzed keratin from wool, or hydrolyzed keratin from feather that has a number average molecular weight of 500 to 2000.

The silicone composition may also comprise components other than silicone and the granular composite. Examples of the components include a curing agent. As the curing agent, for example, those known as a silicone rubber curing agent can be used. Further, the shape of the silicone composition is not particularly limited. Examples include a film shape.

The terms "comprising" (and "containing") includes the meanings of "consisting essentially of" and "consisting of."

EXAMPLES

The present invention is described in more detail below. However, the present invention is not limited to the following Examples.

1. Various Keratin Treatment on Zinc Oxide Particles

Example 1

Cationized Hydrolyzed Keratin Treatment on XZ-1000F (5 Mass %)

One hundred and fifty grans of hexagonal plate-shaped zinc oxide having a particle diameter of 0.66 µm (XZ-1000F, produced by Sakai Chemical Industry Co., Ltd.) was added to 750 g of water, and the mixture was sufficiently stirred to thus obtain an aqueous slurry having a zinc oxide concentration of 193 g/l. Subsequently, while stirring the slurry, 52.6 g of a cationized hydrolyzed keratin aqueous solution (purity: 15%) (steardimonium hydroxypropyl hydrolyzed keratin: Promois WK-SAQ, produced by Seiwa Kasei Co., Ltd.) was added such that the amount of keratin added to 95 mass % of zinc oxide was 5 mass %. After the resulting product was aged as is for 60 minutes, filtration, washing with water, and drying at 40° C. for 16 hours were performed, thus yielding a granular composite comprising keratin and zinc oxide particles, and having a primary particle diameter of 0.67 µm. The size and morphology of the obtained granular composite were observed with a JSM-6510A scanning electron microscope (produced by JEOL Ltd.).

Example 2

Silylated Hydrolyzed Keratin Treatment on XZ-1000F (5 Mass %)

One hundred and fifty grams of hexagonal plate-shaped zinc oxide having a particle diameter of 0.66 µm (XZ-1000F, produced by Sakai Chemical Industry Co., Ltd.) was added to 750 g of water, and the mixture was sufficiently stirred to thus obtain an aqueous slurry having a zinc oxide concentration of 193 g/l. Subsequently, while stirring the slurry, 31.6 g of a silylated hydrolyzed keratin aqueous solution (purity: 25%) ((dihydroxylmethylsilylpropoxy)hydroxypropyl hydrolyzed keratin: Promois WK-HSIGF produced by Seiwa Kasei Co., Ltd.) was added such that the amount of keratin added to 95 mass % of zinc oxide was 5 mass %. After the resulting product was aged as is for 60 minutes, filtration, washing with water, and drying at 40° C. for 16 hours were performed, thus yielding a granular composite comprising keratin and zinc oxide particles, and having a primary particle diameter of 0.64 µm. The size and morphology of the obtained granular composite were observed with a JSM-6510A scanning electron microscope (produced by JEOL Ltd.).

Example 3

Hydrolyzed Keratin Treatment on XZ-1000F (5 Mass %)

One hundred and fifty grams of hexagonal plate-shaped zinc oxide having a particle diameter of 0.66 µm (XZ-1000F, produced by Sakai Chemical Industry Co., Ltd.) was added to 750 g of water, and the mixture was sufficiently stirred to thus obtain an aqueous slurry having a zinc oxide concentration of 193 g/l. Subsequently, while stirring the slurry, 7.9 g of hydrolyzed keratin powder (produced by Seiwa Kasei Co., Ltd.) was added such that the amount of keratin added to 95 mass % of zinc oxide was 5 mass %. After the resulting product was aged as is for 60 minutes, filtration, washing with water, and drying at 40° C. for 16 hours were performed, thus yielding a granular composite comprising keratin and zinc oxide particles, and having a primary particle diameter of 0.63 µm. The size and morphology of the obtained granular composite were observed with a JSM-6510A scanning electron microscope (produced by JEOL Ltd.).

Example 4

Natural Keratin Treatment on XZ-1000F (5 Mass %)

One hundred and fifty grams of hexagonal plate-shaped zinc oxide having a particle diameter of 0.66 µm (XZ-1000F, produced by Sakai Chemical Industry Co., Ltd.) was added to 750 g of water, and the mixture was sufficiently stirred to thus obtain an aqueous slurry having a zinc oxide concentration of 193 g/l. Subsequently, while stirring the slurry, 158.0 g of a natural keratin aqueous solution (purity: 5%) (produced by Seiwa Kasei Co., Ltd.) was added such that the amount of keratin added to 95 mass % of zinc oxide was 5 mass %. After the resulting product was aged as is for 60 minutes, filtration, washing with water, and drying at 40° C. for 16 hours were performed, thus yielding a granular composite comprising keratin and zinc oxide particles, and having a primary particle diameter of 0.66 µm. The size and morphology of the obtained granular composite were observed with a JSM-6510A scanning electron microscope (produced by JEOL Ltd.).

Example 5

Cationized Hydrolyzed Keratin Treatment on XZ-1000F (1 Mass %)

One hundred and fifty grams of hexagonal plate-shaped zinc oxide having a particle diameter of 0.66 µm (XZ-1000F, produced by Sakai Chemical Industry Co., Ltd.) was added to 750 g of water, and the mixture was sufficiently stirred to thus obtain an aqueous slurry having a zinc oxide concentration of 193 g/l. Thereafter, while stirring the slurry, 10.1 g of a cationized hydrolyzed keratin aqueous solution (purity: 15%) (steardimonium hydroxypropyl hydrolyzed keratin: Promois WK-SAQ, produced by Seiwa Kasei Co., Ltd.) was added such that the amount of keratin added to 99 mass % of zinc oxide was 1 mass %. After the resulting product was aged as is for 60 minutes, filtration, washing with water, and drying at 40° C. for 16 hours were performed, thus yielding a granular composite comprising keratin and zinc oxide particles, and having a primary particle diameter of 0.70 µm. The size and morphology of the obtained granular composite were observed with a JSM-6510A scanning electron microscope (produced by JEOL Ltd.).

Example 6

Cationized Hydrolyzed Keratin Treatment on XZ-1000F (10 Mass %)

A granular composite comprising keratin and zinc oxide particles were obtained in the same manner as in Examples 1 and 5, except that the amount of keratin added to 90 mass % of zinc oxide was changed to 10 mass %. Then, the morphology was observed, and the physical properties were evaluated.

Example 7

Cationized Hydrolyzed Keratin Treatment on XZ-1000F (20 Mass %)

A granular composite comprising keratin and zinc oxide particles were obtained in the same manner as in Examples 1 and 5, except that the amount of keratin added to 80 mass % of zinc oxide was changed to 20 mass %. Then, the morphology was observed, and the physical properties were evaluated.

Example 8

Cationized Hydrolyzed Keratin Treatment on XZ-3000F (5 Mass %)

One hundred and fifty grams of hexagonal plate-shaped zinc oxide having a particle diameter of 2.08 µm (XZ-3000F, produced by Sakai Chemical Industry Co., Ltd.) was added to 750 g of water, and the mixture was sufficiently stirred to obtain an aqueous slurry having a zinc oxide concentration of 193 g/l. Thereafter, while stirring the slurry, 52.6 g of a cationized hydrolyzed keratin aqueous solution (purity: 15%) (steardimonium hydroxypropyl hydrolyzed keratin: Promois WK-SAQ, produced by Seiwa Kasei Co., Ltd.) was added such that the amount of keratin added to 95 mass % of zinc oxide was 5 mass %. After the resulting product was aged as is for 60 minutes, filtration, washing with water, and drying at 40° C. for 16 hours were performed, thus yielding a granular composite comprising keratin and zinc oxide particles, and having a primary particle diameter of 2.15 µm. The size and morphology of the obtained granular composite were observed with a JSM-6510A scanning electron microscope (produced by JEOL Ltd.).

Comparative Example 1

No Treatment on XZ-1000F

Hexagonal plate-shaped zinc oxide (XZ-1000F, produced by Sakai Chemical Industry Co., Ltd.) was used as particles for comparison. The primary particle diameter was 0.66 µm. The morphology of the particles was observed with a JSM-6510A scanning electron microscope (produced by JEOL Ltd.). As is clear from the above description, the particles here are zinc oxide particles that serve as the matrix or the granular composites comprising, keratin and zinc oxide particles obtained in Examples 1, 2, 3, 4 and 5.

Comparative Example 2

No Treatment on XZ-3000F

Hexagonal plate-shaped zinc oxide (XZ-3000F, produced by Sakai Chemical Industry Co., Ltd.) was used as particles for comparison. The primary particle diameter was 2.08 µm. The morphology of the particles was observed with a JSM-6510A scanning electron microscope (produced by JEOL Ltd.). The particles here are zinc oxide particles that serve as the matrix of the granular composite comprising keratin and zinc oxide particles obtained in Example 6.

Comparative Example 3

Amorphous Zinc Oxide Particles

Amorphous zinc oxide (Zinc Oxide No. 1: JIS standard, produced by Sakai Chemical Industry Co., Ltd.) was used as particles for comparison. The primary particle diameter was 0.48 µm. The morphology of the particles was observed with a JSM-6511A scanning electron microscope (produced by JEOL Ltd.).

Measurement of MIU (Mean Frictional Coefficient)

The MIU (mean frictional coefficient) value of the granular composites comprising keratin and hexagonal plate-shaped zinc oxide particles was measured using a KES-SE friction tester (produced by Kato Tech Co., Ltd.). Specifically, a 25-mm wide double-sided tape was applied to a slide glass, the granular composite (powder) was placed thereon and spread with a makeup puff, and the MIU (mean frictional coefficient) was measured with a KES-SE friction tester (produced by Kato Tech Co., Ltd.). The measurement was performed under the conditions of a friction measurement load of 25 gf, a surface measurement sample moving speed of 1 mm/sec, and a measurement distance range of 20 mm. As the sensor, a silicone contactor (silicone rubber friction element with unevenness assuming a human finger) was used.

Measurement of MMD Mean Deviation of Frictional Coefficient)

The MMD (mean deviation of frictional coefficient) value of the granular composites comprising keratin and hexagonal plate-shaped zinc oxide particles was measured using a KES-SE friction tester (produced by Kato Tech Co., Ltd.). Specifically, a 25-mm wide double-sided tape was applied to a slide glass, the granular composite (powder) was placed thereon and spread with a makeup puff, and the MMD (mean deviation of frictional coefficient) was measured with a KES-SE friction tester (produced by Kato Tech Co., Ltd.). The measurement was performed under the conditions of a friction measurement load of 25 gf, a surface measurement sample moving speed of 1 mm/sec, and a measurement distance range of 20 mm. As the sensor, a silicone contactor (silicone rubber friction element with unevenness assuming a human finger) was used.

Measurement of Primary Particle Diameter

The primary particle diameter of hexagonal plate-shaped zinc oxide particles and granular composite is a value calculated from 50% in the cumulative distribution obtained by measuring the diagonal diameter (μm) of 100 particles in the visual field of a photograph taken at 2000 to 50000-fold magnification with a scanning electron microscope (SEM) (JSM-6510A, produced by JEOL Ltd.) (if the hexagonal plate-shaped zinc oxide particles or the granular composite have a hexagonal plate shape, then a length of a single diagonal line arbitrarily selected from three diagonal lines of the hexagonal plate-shaped surface).

The primary particle diameter of the amorphous particles is a value calculated from 50% in the cumulative distribution obtained by measuring the particle diameter (μm) of 100 particles defined by an average diameter based on the X-Y axes in the visual field of a photograph taken at 2000 to 50000-fold magnification with a scanning electron microscope (SEM) (JSM-6510A, produced by JEOL Ltd.) (an average length of the interval between two parallel lines sandwiching a particle along the X axis direction, and the interval between two parallel lines sandwiching the particle along the Y axis direction).

Measurement of Keratin Content in Granular Composite

Two grams each of the granular composite and the hexagonal plate-shaped zinc oxide particles used as a raw material of the granular composite were placed separately in a crucible, and heated at 500° C. for 1 hour in an electric furnace. After heating, each of the weights was measured. Then, the keratin content (mass %) of the granular composite was calculated, assuming that the keratin contained in the granular composite completely disappeared and that the reduction rate of the hexagonal plate-shaped zinc oxide particles (raw material) was the same in both of these cases.

Measurement of Spectral Reflectance

The spectral reflectance was measured with a spectrophotometer (V-570, produced by JASCO Corporation). More specifically, the granular composites or particles obtained in the Examples and Comparative Examples were placed in the dedicated cells, and mounted on the spectrophotometer to determine the spectral reflectance at each wavelength. Since the reflectance equals "100−absorption rate," higher absorption means lower reflectance, which is preferable.

Figure 2:
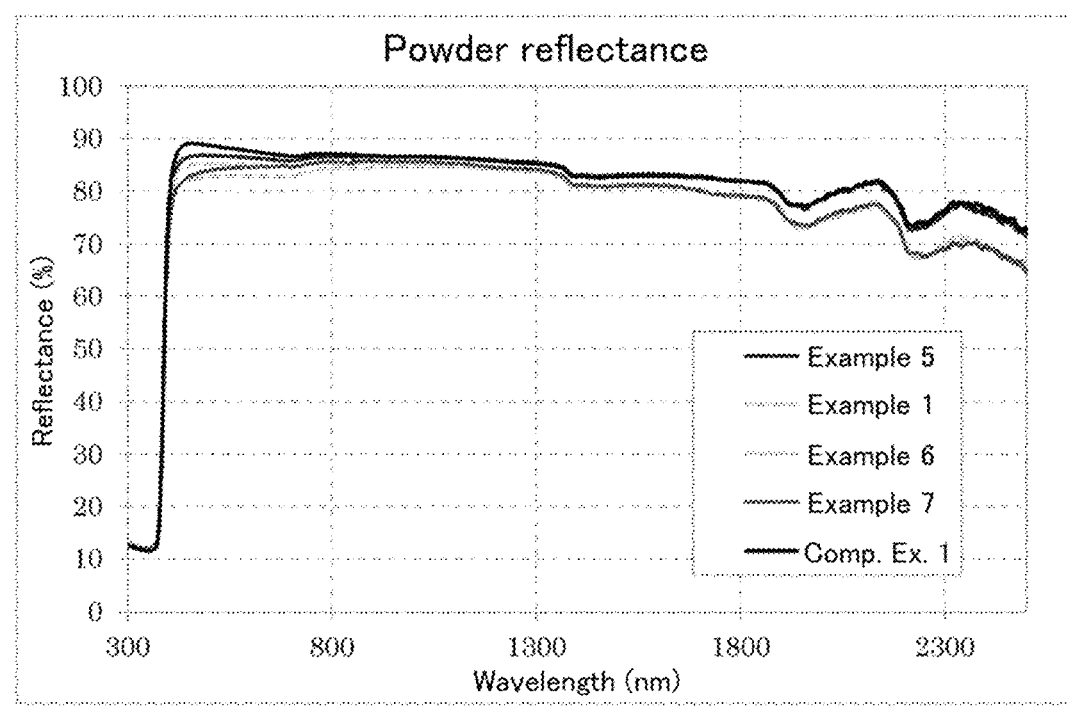
FIG. 2 is a graph showing the measurement results of spectral reflectance of granular composites comprising keratin and hexagonal plate-shaped zinc oxide particles, and hexagonal plate-shaped zinc oxide particles themselves.

FIGS. 6-8 show the analytical results above. The figures also show the evaluation results of the physical properties of the obtained particles. The figures also show the number average molecular weight of each keratin used. FIGS. 1 and 2 show the spectral reflectance measurement results.

2. Various Keratin Treatment on Zinc Oxide Particles

TABLE 4

|  | Keratin sample No. | State | Origin | Keratin content (mass %) | Structure of contained keratin | Number average molecular weight | Solvent | Purchased from |
| --- | --- | --- | --- | --- | --- | --- | --- | --- |
| Ref. Ex. 1a | Keratin sample ① | Liquid | Wool | 5% | Natural keratin | 40,000 | Water | Croda Japan KK |
| Ref. Ex. 2a | Keratin sample ② | Liquid | Wool | 25% | Hydrolyzed keratin | 400 | Water | Seiwa Kasei Co., Ltd. |
| Ref. Ex. 3a | Keratin sample ③ | Liquid | Wool | 25% | Hydrolyzed keratin | 1,000 | Water | |
| Ref. Ex. 4a | Keratin sample ④ | Liquid | Wool | 20% | Hydrolyzed keratin | 4,000 | Water | |
| Ref. Ex. 5a | Keratin sample ⑤ | Liquid | Wool | 20% | Hydrolyzed keratin | 10,000 | Water | |
| Ref. Ex. 6a | Keratin sample ⑥ | Liquid | Wool | 10% | Hydrolyzed keratin | 30,000 | Water | |
| Example 4a | Keratin sample ⑦ | Liquid | Wool | 25% | Cationized hydrolyzed keratin (hydroxypropyltrimonium hydrolyzed keratin) | 1,200 | Water | |
| Example 1a | Keratin sample ⑧ | Liquid | Wool | 15% | Cationized hydrolyzed keratin (steardimonium hydroxypropyl hydrolyzed keratin) | 800 | Water | |
| Example 2a | Keratin sample ⑨ | Liquid | Wool | 25% | Silylated hydrolyzed keratin ((dihydroxymethylsilyl-propoxy)hydroxypropyl hydrolyzed keratin) | 1,200 | Water | |
| Ref. Ex. 7a | Keratin sample ⑩ | Liquid | Wool | 20% | Hydrolyzed keratin | 20,000-30,000 | Water | Ichimaru Pharcos Co. Ltd. |
| Ref. Ex. 8a | Keratin sample ⑪ | Liquid | Wool | 20% | Cationized hydrolyzed keratin (hydroxypropyltrimonium hydrolyzed keratin) | 20,000-30,000 | Water | |
| Ref. Ex. 9a | Keratin sample ⑫ | Liquid | Wool | 10% | Cationized hydrolyzed keratin (lauryldimonium hydroxypropyl hydrolyzed keratin) | 20,000-30,000 | Water | |
| Ref. Ex. 10a | Keratin sample ⑬ | Liquid | Wool | 10% | Hydrolyzed keratin | 25,000-35,000 | Water | |

TABLE 4-continued

| Keratin sample No. | State | Origin | Keratin content (mass %) | Structure of contained keratin | Number average molecular weight | Solvent | Purchased from |
|---|---|---|---|---|---|---|---|
| Ref. Ex. 11a Keratin sample ⑭ | Liquid | Wool | 10% | Cationized hydrolyzed keratin (hydroxypropyltrimonium hydrolyzed keratin) | 25,000-35,000 | Water | |
| Example 3a Keratin sample ⑮ | Powder | Feather | 100% | Hydrolyzed keratin | 750 | — | Toyo Feather Industry Co., Ltd. |

The surface of hexagonal plate-shaped zinc oxide particles was treated using various keratins shown in Table 4. More specifically, the treatment was performed as follows. One hundred and fifty grams of hexagonal plate-shaped zinc oxide having a particle diameter of 0.66 µm (XZ-1000F, produced by Sakai Chemical Industry Co., Ltd.) was added to 750 g of water, and the mixture was sufficiently stirred to thus obtain an aqueous slurry having a zinc oxide concentration of 193 g/l. Subsequently, while stirring the slurry, various keratins shown in Table 4 were added such that the amount of each keratin added to 95 mass % of zinc oxide was 5 mass % (the amount added was calculated from the keratin content of the various keratin samples). After the resulting product was aged as is for 60 minutes, filtration, washing with water, and drying at 40° C. for 16 hours were performed, thus yielding granular composites comprising keratin and zinc oxide particles (the Examples and the Reference Examples: Table 4).

As is clear from the descriptions of Examples 1 to 4 and Table 4, Example 1 is the same as Example 1a, Example 2 is the same as Example 2a, Example 3 is the same as Example 3a, and Example 4 is the same as Reference Example 1a.

The transmittance of the film of each obtained granular composite was measured as follows. Silicone rubber (KE-1300T, produced by Shin-Etsu Chemical Co., Ltd.) (4.27 g) and a curing agent (CAT-1300, produced by Shin-Etsu Chemical Co., Ltd.) (0.47 g) were mixed, and 0.25 g of the granular composite powders were each individually added, followed by kneading by a Hoover muller. The resulting product was applied to a TAC film using a 1-miL applicator (25.4 µm), and allowed to stand to dry overnight. The transmittance of each film obtained after drying was measured with a spectrophotometer.

Figure 3:
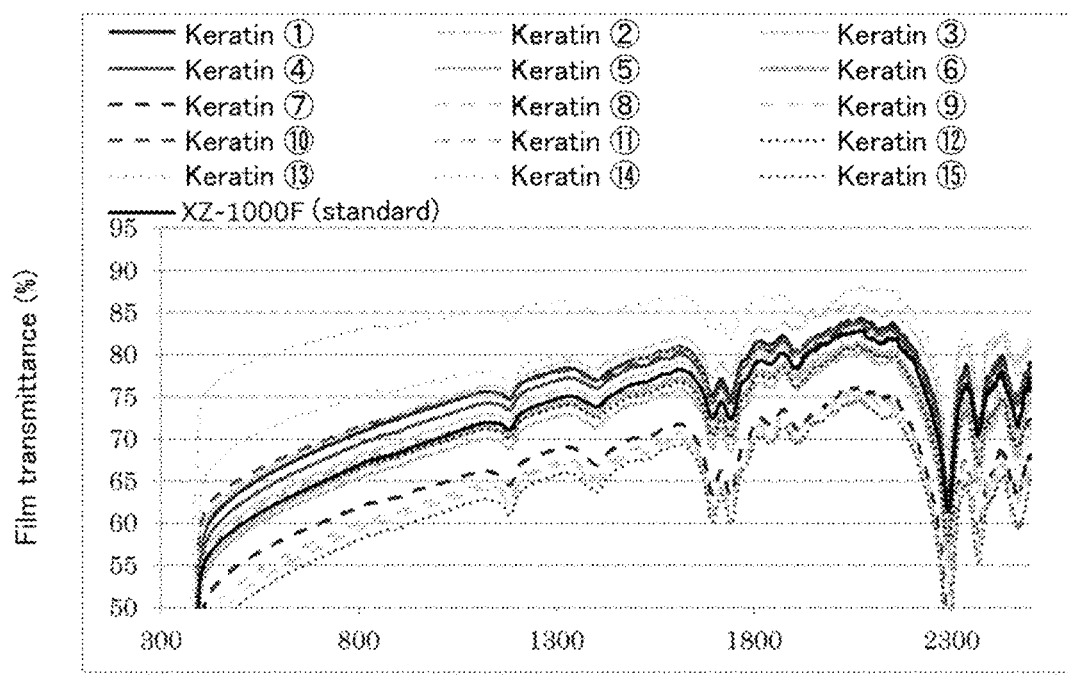
FIG. 3 is a graph showing the measurement results of the shielding ratio of dry coating films prepared by mixing silicone rubber with various granular composites comprising keratin and hexagonal plate-shaped zinc oxide particles, or with hexagonal plate-shaped zinc oxide particles themselves.
Figure 4:
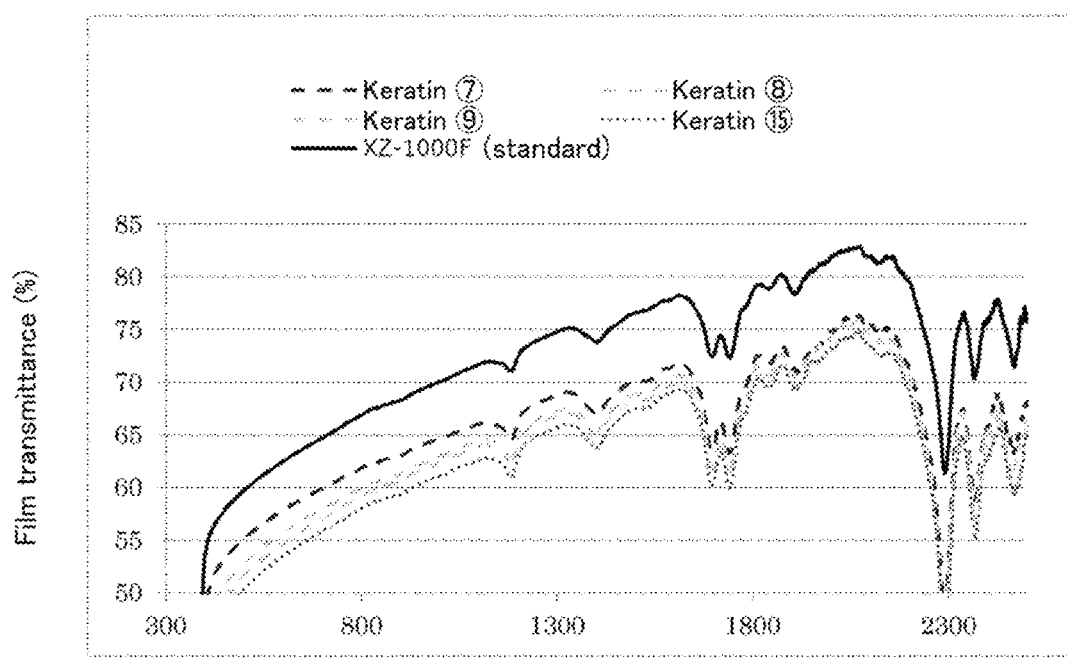
FIG. 4 is a graph showing the measurement results of the shielding ratio of dry coating films prepared by mixing silicone rubber with various granular composites comprising keratin and hexagonal plate-shaped zinc oxide particles, or with hexagonal plate-shaped zinc oxide particles themselves.

FIG. 3 shows the results. The lower the transmittance, the higher the shielding effect. FIG. 4 is a graph showing the results of granular composites that have particularly low transmittance from among the granular composites shown in FIG. 3 (i.e., those having significantly lower transmittance than zinc oxide particles XZ-1000F themselves).

Table 4, FIG. 3, and FIG. 4 reveal that when the cationized hydrolyzed keratin from wool, silylated hydrolyzed keratin from wool, or hydrolyzed keratin from feather that had a number average molecular weight of about 500 to 2000 was used as keratin for treating hexagonal plate-shaped zinc oxide particles, the resulting granular composite, when mixed with silicone to form a silicone composition, had a particularly excellent near-infrared shielding effect.

Analysis of Properties of Each Granular Composite

The size and morphology of the granular composites of Examples 1a to 4a were observed with a JSM-6510A scanning electron microscope (produced by JEOL Ltd.). Further, in the same manner as described above, the MIU, MMD, primary particle diameter, and keratin content of the granular composite were measured. FIG. 9 shows the measurement results.

3. Various Keratin Treatment on Zinc Oxide Particles

Figure 5:
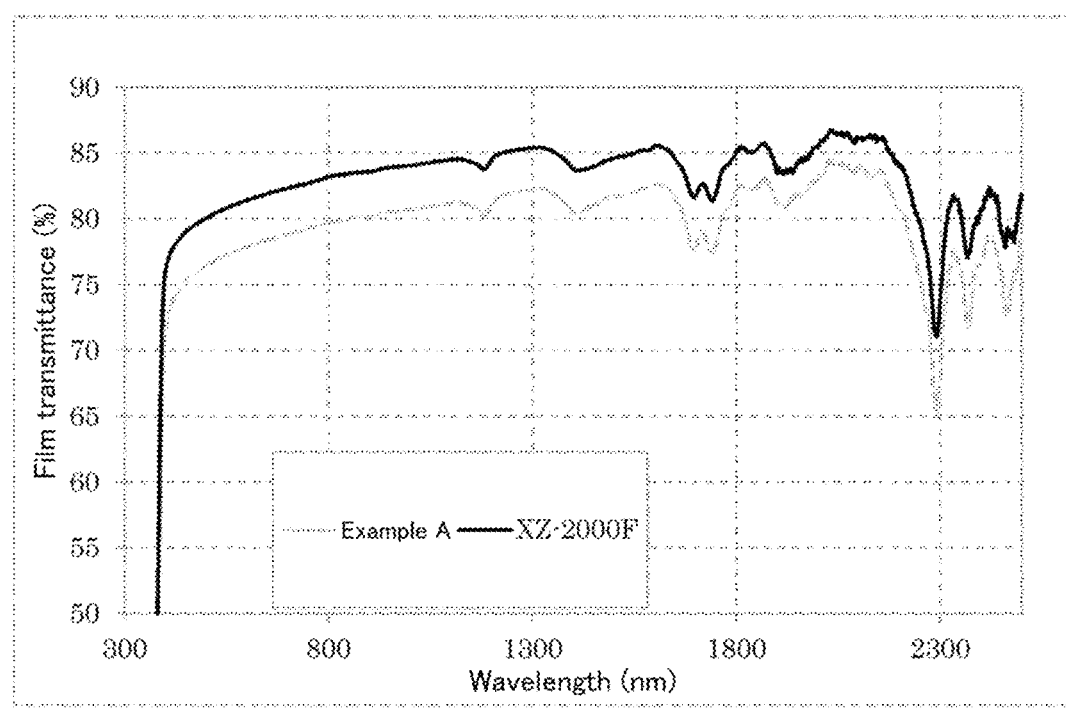
FIG. 5 is a graph showing the measurement results of the shielding ratio of dry coating films prepared by mixing silicone rubber with a granular composite comprising keratin and hexagonal plate-shaped zinc oxide particles, or with hexagonal plate-shaped zinc oxide particles themselves.

A granular composite was prepared in the same manner as above, except that the keratin used in the preparation of the granular composite of Example 2a was used as the keratin, and hexagonal plate-shaped zinc oxide having a particle diameter of 1.52 µm (XZ-2000F, produced by Sakai Chemical Industry Co., Ltd.) was used as the hexagonal plate-shaped zinc oxide particles (Example A). The transmittance of the film of the obtained granular composite was measured in the same manner as described above. FIG. 5 shows the results. Additionally, in the same manner as described above, the MIU, MMD, primary particle diameter, and keratin content of the obtained granular composite were measured. FIG. 10 shows the measurement results.

The invention claimed is:

1. A granular composite comprising keratin and hexagonal plate-shaped zinc oxide particles having a primary particle diameter of 0.1 µm to 5 µm as measured by a scanning electron microscopy at 2,000 to 50,000-fold magnification.

2. The granular composite according to claim 1, wherein the keratin is present on the surface of the hexagonal plate-shaped zinc oxide particles.

3. The granular composite according to claim 1, wherein the keratin is at least one member selected from the group consisting of natural keratin, hydrolyzed keratin, cationized hydrolyzed keratin, and silylated hydrolyzed keratin.

4. The granular composite according to claim 1, wherein the keratin content is 0.05 to 5 mass %.

5. The granular composite according to claim 1, wherein the keratin is at least one member selected from the group consisting of cationized hydrolyzed keratin from wool, silylated hydrolyzed keratin from wool, and hydrolyzed keratin from feather; and has a number average molecular weight of 500 g/mol to 2000 g/mol.

6. An external composition comprising the granular composite of claim 1.

7. The external composition according to claim 6, which is a cosmetic composition, a quasi-drug composition, or a pharmaceutical composition.

8. A composition comprising the granular composite of claim 5 and silicone.

9. A film comprising the granular composite of claim 5 and silicone.

10. The granular composite according to claim 2, wherein the keratin is at least one member selected from the group consisting of natural keratin, hydrolyzed keratin, cationized hydrolyzed keratin, and silylated hydrolyzed keratin.

11. The granular composite according to claim 2, wherein the keratin content is 0.05 to 5 mass %.

12. The granular composite according to claim 2, wherein the keratin is at least one member selected from the group consisting of cationized hydrolyzed keratin from wool, silylated hydrolyzed keratin from wool, and hydrolyzed keratin from feather; and has a number average molecular weight of 500 g/mol to 2000 g/mol.

13. An external composition comprising the granular composite of claim 2.

14. The external composition according to claim 6, which is a cosmetic composition.

15. An external composition comprising the granular composite of claim 5.

16. An external composition comprising the granular composite of claim 12.

17. A cosmetic composition comprising the granular composite according to claim 1, wherein the keratin is present on the surface of the hexagonal plate-shaped zinc oxide particles.

18. The cosmetic composition according to claim 17, wherein the keratin is at least one member selected from the group consisting of natural keratin, hydrolyzed keratin, cationized hydrolyzed keratin, and silylated hydrolyzed keratin.

* * * * *